United States Patent [19]

Mitchell et al.

[11] Patent Number: 4,909,997
[45] Date of Patent: Mar. 20, 1990

[54] TETRABROMOBISPHENOL-A PROCESS

[75] Inventors: Olan W. Mitchell, Magnolia, Ark.; Bonnie G. McKinnie, Baton Rouge, La.

[73] Assignee: Ethyl Corporation, Richmond, Va.

[21] Appl. No.: 205,729

[22] Filed: Jun. 13, 1988

Related U.S. Application Data

[60] Division of Ser. No. 125,931, Nov. 27, 1987, Pat. No. 4,783,556, which is a continuation of Ser. No. 870,813, Jun. 5, 1986, abandoned, which is a continuation-in-part of Ser. No. 778,710, Sep. 23, 1985, Pat. No. 4,628,124.

[51] Int. Cl.$^4$ .............................................. B01J 5/06
[52] U.S. Cl. .................................... 422/225; 422/234; 366/178
[58] Field of Search ................ 422/225, 234; 137/896; 366/150, 177, 178

[56] References Cited

U.S. PATENT DOCUMENTS 3,182,088  5/1965  Hennis .................................. 260/619
3,868,423  2/1975  Montanari et al. .................. 260/619
4,112,242  9/1978  Swietoslawski et al. ........... 568/726
4,451,675  5/1984  Bounds ................................ 568/726

FOREIGN PATENT DOCUMENTS 2005259  8/1971  Fed. Rep. of Germany .
949306  2/1964  United Kingdom .

Primary Examiner—Barry S. Richman
Assistant Examiner—D. John Griffith, Jr.
Attorney, Agent, or Firm—Edgar E. Spielman, Jr.

[57] ABSTRACT

Tetrabromobisphenol-A is made in high purity by adding a methanol-bromine solution to a methanol-bisphenol-A solution with vigorous agitation. Use of the bromine-methanol solution reduces the amount of by-products compared to the use of liquid bromine feed to a methanol-bisphenol-A solution. The process is readily adapted to large scale equipment by circulating the reaction mixture from the reaction vessel through an external closed loop which includes an impingement mixer. The bromine-methanol feed is pumped at the proper rate and ratio into the impingement mixture whereby it impinges with the circulating reaction mixture. The resultant bromination mixture is then returned to the reaction vessel.

3 Claims, 1 Drawing Sheet

TETRABROMOBISPHENOL-A PROCESS

This application is a division of application Ser. No. 125,931, filed Nov. 27, 1987, now U.S. Pat. No. 4,783,556, which in turn is a continuation of application Ser. No. 870,813, filed June 5, 1986, now abandoned, which in turn is a continuation-in-part of application Ser. No. 778,710, filed Sept. 23, 1985, now U.S. Pat. No. 4,628,124.

BACKGROUND OF THE INVENTION

Tetrabromobisphenol-A (hereinafter "TBBP-A") is 4,4'-isopropylidenebis(2,6-dibromophenol). It is a widely used commercial fire retardant. There have been numerous publications on how it can be made. Hennis, U.S. Pat. No. 3,234,289, describes a process in which bisphenol-A (i.e. 4,4'-isopropylidenebisphenol) is placed in a water-alcohol mixture and liquid bromine is added at 22°–28° C. followed by reflux. Majewski et al., U.S. Pat. No. 3,363,007, discloses a process for brominating bisphenol-A in a mixture of water and an alkyl ether of a lower glycol.

Asadorian et al., U.S. Pat. No. 3,546,302, discloses a bromination process conducted in a two-phase solvent having an aqueous phase and an organic phase.

Montanari et al., U.S. Pat. No. 3,868,423, discloses the bromination of isopropylidenebisphenol with liquid bromine and gaseous chlorine in a methanol solvent. Janzon et al., U.S. Pat. No. 3,929,907, discloses the bromination of bisphenols in the presence of aqueous hydrogen peroxide.

Brackenridge, U.S. Pat. No. 4,013,728, teaches a process for brominating bisphenol-A in aqueous acetic acid followed by a heating step. Jenkner, U.S. Pat. No. 4,036,894, discloses bromination of bisphenol-A in acetic acid with recycle of the mother liquor and addition of alkaline or alkaline earth metal acetate.

Production of TBBP-A by dissolving bisphenol-A in methanol and adding liquid bromine is an effective way to make TBBP-A but the product contains various impurities which detract from its commercial value. These impurities include brominated phenols and hydrolyzable impurities. A need exists for a process that would lower the amount of these impurities.

SUMMARY OF THE INVENTION

It has been discovered that the amount of impurities in TBBP-A can be sharply decreased by using a process in which bisphenol-A is dissolved in methanol and brominated by adding a solution of bromine in methanol to the bisphenol-A/methanol solution. It has been shown that the amount of impurities can be sharply reduced from about 4 weight percent down to as little as 0.2 weight percent. It has now been discovered that adaptation of this process into large scale equipment can be facilitated by pre-mixing the bromine-methanol feed and impinging this feed stream with a stream of the reaction mixture being circulated outside the reaction vessel through a closed loop.

DESCRIPTION OF THE PREFERRED EMBODIMENTS

Figure 1:
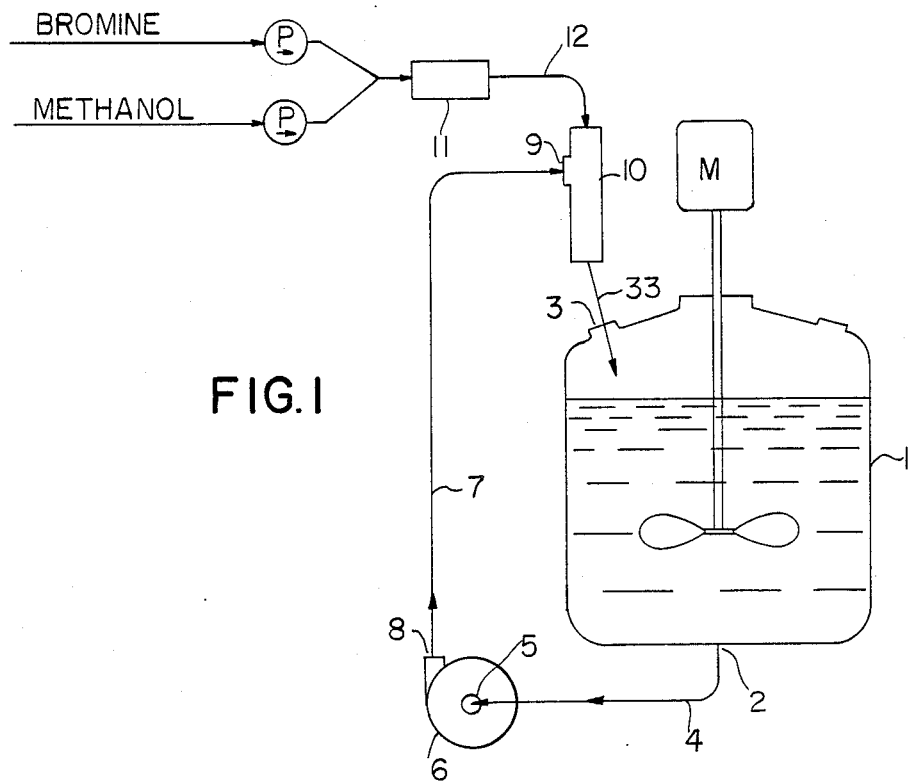
FIG. 1 is a schematic representation of an embodiment of the process showing the reaction vessel and the external closed loop flow path through an impingement mixer.
Figure 2:
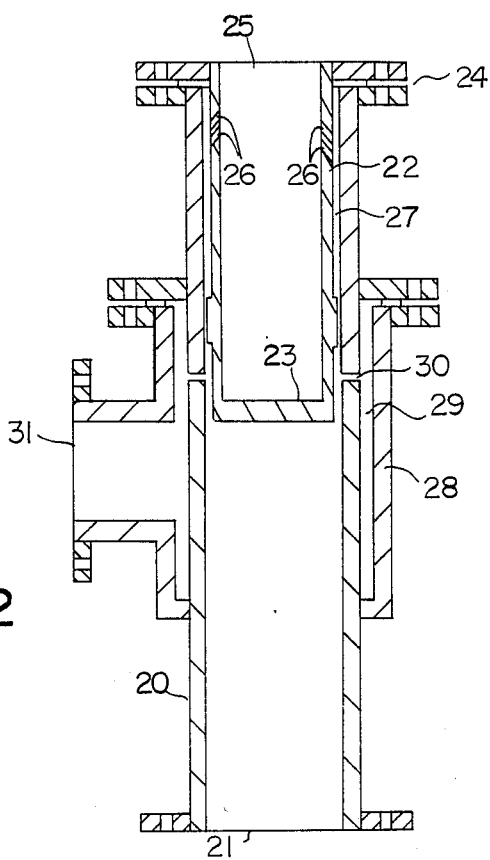
FIG. 2 is a cross-section of a suitable impingement mixer in which pre-mixed bromine-methanol feed is impinged with circulating reaction mixture in an annular space.

A preferred embodiment of the invention is a process for making TBBP-A in high yield and high purity, said process comprising:
  (A) dissolving disphenol-A in methanol in a reaction vessel,
  (B) withdrawing a stream of the bisphenol-A/methanol solution from said reaction vessel and feeding this withdrawn stream to an impingement mixer,
  (C) feeding a mixture of bromine and methanol to said impingement mixer,
  (D) impinging said stream of bisphenol-A/methanol solution with said mixture of bromine and methanol in said impingement mixture forming a bromination mixture and
  (E) conducting said bromination mixture back into said reaction vessel,
  (F) continuing steps (B), (C), (D) and (E) until the desired amount of bromine has been fed and
  (G) recovering tetrabromobisphenol-A.

Initially a reaction vessel 1, preferably glass or glass-lined, is charged with methanol and bisphenol-A. The amount of methanol used to dissolve the bisphenol-A can vary over a wide range. A useful range is about 1.0–6 parts by weight methanol per each part bisphenol-A. A more preferred range is about 1.5–3 parts by weight methanol per each part bisphenol-A and the most preferred amount is about 2.0 parts methanol per each part bisphenol-A.

The process is then started by activating pump 6 which withdraws reaction mixture (initially methanol-bisphenol-A solution) from bottom outlet 2 through outlet conduit 4. Pump 6 is preferably of the centrifugal type and receives the reaction mixture at suction intake 5. The reaction mixture is pumped through discharge port 8 and riser conduit 7 to impingement mixer 10 which will be described in detail later.

Concurrently bromine and methanol are pumped at a controlled rate from storage through conventional static mixer 11.

The bromine/alcohol ratio can vary widely. The more dilute the bromine solution, the better the results. However, excessive dilution causes an unacceptable drop in production per unit volume of reactor. A useful range in which to operate is about 1–4 parts by weight bromine per each part methanol. A more preferred range is about 1–3 parts bromine per each part methanol. The most preferred amount is about 2 parts bromine per each part methanol.

The ratio of (1) the volume of the reaction mixture recirculation through the external loop and impingement mixer to (2) the volume of the methanol-bromine solution feed can vary over a wide range. Preferably the volume of the reaction mixture recirculation will exceed the volume of the methanol-bromine feed. A useful range is about 0.8–30:1. A more useful range is about 10–20:1 and a most preferred range is about 15–18:1.

The amount of methanol-bromine solution should be an amount that supplies sufficient bromine to make an acceptable product. The stoichiometric requirement is 4 moles of bromine per mole of bisphenol-A. A useful range in which to operate is about 3.9–4.5 moles of bromine per mole of bisphenol-A and the most preferred range is 4.0–4.1 moles bromine per mole of bisphenol-A.

From static mixer 11 the bromine-methanol solution passes through conduit 12 to impingement mixer 10.

Impingement mixer 10 comprises an outer substantially cylindrical shell 20 open at its discharge end 21. Hollow distribution member 22, essentially closed at one end 23, is axially located inside shell 20 and sealably engaged with shell 20 at end 24 opposite discharge end 21. Distribution member 22 has an inlet 25 and a plurality of orifices 26 circumferentially located in the sidewall of member 22 forming a plurality of passages from the hollow interior of member 22 into annular space 27 between member 22 and shell 20.

Outer axial cylindrical member 28 is sealably engaged at both ends to shell 20 forming outer annular chamber 29. A circumferential slit 30 extends around shell 20 forming a narrow circumferential passage from annular chamber 29 into annular space 27. Side inlet 31 in member 28 is adapted to connect to riser conduit 7 to receive the reaction mixture.

The bromine-methanol solution from static mixer 11 passes through conduit 12 to inlet 25 of distribution member 22. The bromine-methanol solution is forced at high velocity through orifice 26 into annular space 27. Meanwhile reaction mixture from riser conduit 7 enters annular chamber 29 through side inlet 31 and is forced at high velocity through slit 30 into annular space 27.

The bromine-methanol solution and the reaction mixture impinge in annular space 27 and the resultant mixture passes through discharge end 21 which is operably connected to feed conduit 33 which feeds the mixture back into reactor 1.

The improvements of the present process enable the production of TBBP-A on a large scale at high yield to give a product that is substantially lower in impurities compared to TBBP-A made feeding bromine to a methanol-bisphenol-A solution.

Rapid mixing of the bromine-methanol and bisphenol-A-methanol is highly preferred in order to obtain the best results with the new mode of bromine addition. The present process is a facile way of providing the high agitation mentioned in our prior application Ser. No. 778,710.

The bromine-methanol solution may be fed to the circulating reaction mixture at an initial temperature that is ambient or lower although this is not essential. For example the bromine-methanol feed can be started while the reactor contents and circulating reaction mixture is at temperatures from −10° up to about 30° or somewhat higher if that is what the liquid happens to be at. As the feed progresses the temperature will rise due to the heat of the reaction. Sometime during the feed the reactor temperature will attain reflux conditions and reflux can be continued through the end of the feed of the bromine-methanol solution although reflux is not essential as long as the reaction is continued long enough to substantially complete the bromination. After this, heat can be applied to maintain reflux for a short period of time of say 10 minutes to 1 hour to assure completion of the reaction.

During the bromine-methanol feed, the bromination of bisphenol-A forms HBr which reacts with the methanol to form methyl bromide. The methyl bromide vaporizes and can be collected from the off-gas and marketed as a commercial product for its many known uses such as soil fumigation.

TBBP-A can be recovered from the reaction mixture using conventional methods. For example the final reaction mixture can be diluted with water and filtered to recover the TBBP-A. The product can then be dried in an oven to remove water, methanol, bromine, HBr and other volatiles.

The following examples serve to illustrate how the process is carried out and to compare it to a prior art process using liquid bromine feed rather than feeding a bromine-methanol solution.

EXAMPLE 1

Comparative Example

In a reaction vessel fitted with a condenser, heating mantle, thermometer, stirrer and addition funnel with a dip tube was placed 223 grams of methanol (3% water) and 52.65 grams bisphenol-A. While stirring, this was heated to reflux and 154.5 grams of bromine was added through the dip leg over an 80 minute period at reflux. Reflux was continued for 8 minutes and then $Na_2SO_3$ was added to destroy unreacted bromine. A small sample of the product was removed and dissolved in methylene chloride, washed with water and dried over anhydrous sodium sulfate. The methylene chloride was evaporated and N,o-bis(trimethylsilyl)trifluoroacetamide added to derivatize the product which was then analyzed by gas chromatography.

EXAMPLE 2

This example was conducted using a feed of bromine-methanol to a methanol-bisphenol-A solution but without the use of an impingement mixer in an exterior circulating closed loop.

A reaction vessel was charged with 54.16 grams bisphenol-A and 122 grams methanol (3% water). A solution of 165 grams bromine in 85 grams methanol was prepared with cooling. While stirring at the same rate as in Example 1, the bromine-methanol solution was added slowly to the bisphenol-A solution starting at room temperature. When one-third of the bromine solution was added, the reaction mixture reached reflux. It was maintained at reflux through the remainder of the feed. Feed time was 84 minutes. Reflux was continued for 8 minutes. Sodium sulfite was added to destroy unreacted bromine. A sample of product was worked-up and derivatived as in Example 1 and analyzed by gas chromatography.

Analysis of the TBBP-A from Examples 1 and 2 is shown in the following table.

| | Amount (area %) | |
| --- | --- | --- |
| Compound | Example 1 | Example 2 |
| TBBP-A | 95.57 | 99.14 |
| Tribromobisphenol-A | 0.05 | 0.277 |
| Dibromobisphenol-A | ND[4] | 0.030 |
| Tribromphenol | 2.5 | 0.188 |
| Dibromophenol | ND | 0.068 |
| Bromphenol | ND | 0.014 |
| Compound A[1] | 0.83 | 0.078 |
| Compound B[2] | 0.22 | 0.036 |
| Compound C[3] | 0.58 | 0.118 |
| Unknown | ND | 0.009 |

[1]1-bromo-2-(3,5-dibromo-4-hydroxyphenyl)-2-methoxypropane.
[2]1,1-dibromo-2-(3,5-dibromo-4-hydroxyphenyl)-2-methoxypropane.
[3]1,3-dibromo-2-(3,5-dibromo-4-hydroxyphenyl)-2-methoxypropane.
[4]ND means present but not determined.

The results show that the tetrabromobisphenol-A made in Example 2 is significantly higher in purity compared to Example 1 made by a prior art process.

The following example shows the use of a bromine-methanol feed as in Example 2 but includes the further improvement of this invention whereby the reaction mixture is circulated through an external closed loop and the bromine-methanol solution is injected into the closed loop in an impingement type mixer.

EXAMPLE 3

In a glass lined reaction vessel was placed 2240 lbs. of methanol and 1000 lbs. of bisphenol-A. When dissolved the solution was circulated through an external loop which included an impingement mixer at the rate of 250 gal. per minute. A bromine-methanol solution (2:1 bromine:methanol weight ratio) was pumped to the impingement mixer at a rate of 249 lbs./min. The bromine solution feed was continued until 1% stoichiometric excess over that required for TTBP-A had been fed. The temperature in the reaction vessel during bromine-methanol feed rose from 22° C. to reflux over 20 min. Reflux was maintained until the bromine-methanol feed was complete. Following feed completion, the recirculation of reaction mixture was stopped and reflux was continued for 30 minutes. The reaction mixture was analyzed as in Example 1 with the results shown in the table below. Product was recovered by quenching with water and filtering.

| Compound | Example 3 | Typical[1] |
|---|---|---|
| TBBP-A | 98.03% | 91–96 |
| Tribromobisphenol-A | 0.09 | 0.5 |
| Tribromophenol | 0.60 | 2.5 |
| Dibromophenol | 0.06 | ND |
| Compound A | 0.24 | |
| Compound B | 0.14 | 1.6 |
| Compound C | 0.30 | |

[1]Typical analysis of TBBP-A made on the same commercial scale but direct liquid bromine feed to the reactor.

The results show that the improved process achieves a very high purity TBBP-A on a commercial scale.

The improved process is applicable to the bromination of other bisphenols. These are compounds of the structure:

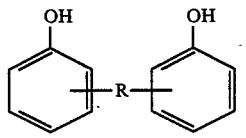

wherein R is a divalent aliphatic hydrocarbon group of 1-4 carbon atoms or a direct bond between the two benzene rings. Representative examples are 4,4'-methylenebisphenol, 2,2'-methylenebisphenol, 2,4'-methylenebisphenol, 4,4'-ethylidenebisphenol, 2,2'-ethylidenebisphenol, 2,4'-ethylidenebisphenol, 2,2'-isopropylidenebisphenol, 2,4'-isopropylidenebisphenol, 4,4'-butylidenebisphenol, 2,2'-butylidenebisphenol, 4,4'-biphenol, 2,2'-biphenol, 2,4'-biphenol and the like. These bisphenols can be substituted for the bisphenol-A, i.e. 4,4'-isopropylidenebisphenol, used in the foregoing description and examples of the present invention. All of the products can be used as fire retardants in a broad range of organic materials normally susceptible to combustion in the presence of air and an ignition source.

We claim:

1. An apparatus adapted to make an organobromine compound in high yield and high purity, said apparatus comprising: a reaction vessel having a bottom outlet and an inlet; a pump; a vessel suitable for containing bromine and a vessel suitable for containing solvent; an annular impingement mixer comprising (1) an outer substantially cylindrical shell, (2) a substantially cylindrical hollow distribution member closed at one end and axially located inside of and spaced apart from said cylindrical shell and sealably engaged with said shell at one end of said shell forming an annular space between said distribution member and said shell, openings in the sidewall of said distribution member forming a flow path from inside said distribution member into said annular space, an end inlet in said distribution member opposite said closed end functioning as an end inlet of said annular impingement mixer, (3) an outer axial cylindrical member around and spaced apart from said cylindrical shell, both ends of said axial cylindrical member being sealably connected to said cylindrical shell forming an annular chamber, said cylindrical shell having fluid passage means around the circumference of said cylindrical shell forming a passage from said annular chamber into said annular space, said outer cylindrical member having an inlet functioning as a side inlet of said annular impingement mixer, said cylindrical shell having an outlet remote from said distribution member; and conduits connecting said parts of said apparatus comprising an outlet conduit forming a flow path from said bottom outlet of said reaction vessel to the intake of said pump, a riser conduit forming a flow path from the discharge port of said pump to said side inlet of said annular impingement mixer, a bromine conduit from said vessel suitable for containing bromine and a solvent conduit from said vessel suitable for containing solvent, said bromine conduit and said solvent conduit being operatively connected to a bromine-solvent conduit, which in turn is connected to said end inlet of said annular impingement mixer, a feed conduit forming a flow path from said outlet of said annular impingement mixer to said inlet of said reaction vessel.

2. An apparatus of claim 1 wherein said vessel suitable for containing solvent is suitable for containing methanol.

3. An apparatus of claim 1 further characterized by having static mixing means in said bromine-solvent conduit.

* * * * *